(12) United States Patent
Hong et al.

(10) Patent No.: US 7,694,550 B2
(45) Date of Patent: Apr. 13, 2010

(54) APPARATUS FOR MEASURING PERMEABILITY RATE OF ANODE OF SOLID OXIDE FUEL CELL

(75) Inventors: Wen-Tang Hong, Caotun Township, Nantou County (TW); Chen-Po Lai, Taoyuan County (TW); Szu-Han Wu, Taoyuan (TW); Hung-Yu Wang, Jhonghe (TW); Ruey-Yi Lee, Longtan Township, Taoyuan County (TW); Chien-Hsiung Lee, Longtan Township, Taoyuan County (TW)

(73) Assignee: Atomic Energy Council, Taoyuan (TW)

( * ) Notice: Subject to any disclaimer, the term of this patent is extended or adjusted under 35 U.S.C. 154(b) by 113 days.

(21) Appl. No.: 12/076,811

(22) Filed: Mar. 24, 2008

(65) Prior Publication Data

US 2009/0151430 A1 Jun. 18, 2009

Related U.S. Application Data

(63) Continuation of application No. 12/000,565, filed on Dec. 13, 2007, now abandoned.

(51) Int. Cl.
*G01N 15/08* (2006.01)
(52) U.S. Cl. ............................................. 73/38
(58) Field of Classification Search .................. 73/38
See application file for complete search history.

(56) References Cited

U.S. PATENT DOCUMENTS

| | | | |
|---|---|---|---|
| 4,531,404 A * | 7/1985 | Phelps et al. .................. 73/38 |
| 5,882,384 A * | 3/1999 | Tom et al. ..................... 96/111 |
| 6,568,282 B1 * | 5/2003 | Ganzi ...................... 73/861.42 |
| 6,570,057 B1 * | 5/2003 | Schmidt et al. ............ 604/378 |
| 7,210,335 B2 * | 5/2007 | Gupta et al. .................... 73/38 |
| 2005/0214604 A1 * | 9/2005 | Goto et al. ..................... 429/22 |
| 2007/0089489 A1 * | 4/2007 | Lewnard et al. ................ 73/38 |
| 2007/0227233 A1 * | 10/2007 | Norenberg ...................... 73/38 |
| 2008/0233010 A1 * | 9/2008 | Blencoe et al. .......... 422/82.12 |

* cited by examiner

*Primary Examiner*—Hezron Williams
*Assistant Examiner*—Mark Shabman
(74) *Attorney, Agent, or Firm*—Jackson IPG PLLC

(57) ABSTRACT

An apparatus is disclosed for measuring the permeability of an anode of a solid oxide fuel cell. The apparatus includes a specimen container, an air reservoir and a recorder. The specimen container includes a can and a cover. The can includes a tunnel defined therein and a cavity in communication with the tunnel. The anode can be disposed in the cavity. The cover includes a tunnel defined therein and a bulger inserted in the cavity and pressed against the anode so that air can penetrate the anode and travel into the tunnel of the can from the tunnel of the cover. The air reservoir is in communication with the cover. The recorder measures and records the pressure and temperature of air in the air reservoir before and after the air is introduced into the specimen container from the air reservoir.

9 Claims, 5 Drawing Sheets

APPARATUS FOR MEASURING PERMEABILITY RATE OF ANODE OF SOLID OXIDE FUEL CELL

This application is a Continuation of application U.S. Ser. No, 12/000,565, entitled "APPARATUS FOR MEASURING PERMEABILITY RATE OF ANODE OF SOLID OXIDE FUEL CELL" and filed on Dec. 13, 2007 now abandoned.

BACKGROUND OF INVENTION

1. Field of Invention

The present invention relates to a solid oxide fuel cell and, more particularly, to an apparatus of measuring the permeability of an anode of a solid oxide fuel cell.

2. Related Prior Art

A solid oxide fuel cell includes a solid electrolyte for separating an anode and a cathode. At the cathode, oxygen is turned into ions. The ions are transferred to the anode from the cathode via the solid electrolyte. At the anode, the ions react with hydrogen and releases electricity. The permeability of the anode influences the performance of the solid oxide fuel cell. In general, the anode is selected before the solid electrolyte and the cathode are selected. An anode will be selected only if the permeability thereof is acceptable.

However, the permeability of an anode is calculated based on the properties of the material of which the anode is made. There has not been any practical apparatus for measuring the permeability of an anode.

A Brugger's Gpp-C can be used to measure the permeability of an anode. A Brugger's Gpp-C however requires a vacuum pump to create vacuum so that the permeability of an anode can be measured.

A He-detector can only detect the leak of a system, but cannot measure the permeability of an anode.

The present invention is therefore intended to obviate or at least alleviate the problems encountered in prior art.

SUMMARY OF INVENTION

The primary objective of the present invention is to provide an apparatus for measuring the permeability of an anode.

To achieve the foregoing objective of the present invention, an apparatus includes a specimen container, an air reservoir and a recorder. The specimen container includes a can and a cover. The can includes a tunnel defined therein and a cavity in communication with the tunnel. An anode can be disposed in the cavity. The cover includes a tunnel defined therein and a bulger inserted in the cavity and pressed against the anode so that air can penetrate the anode and travel into the tunnel of the can from the tunnel of the cover. The air reservoir is in communication with the cover. The recorder measures and records the pressure and temperature of air in the air reservoir before and after the air is introduced into the specimen container from the air reservoir.

Other objectives, advantages and features of the present invention will become apparent from the following description referring to the attached drawings.

BRIEF DESCRIPTION OF DRAWINGS

The present invention will be described via detailed illustration of the preferred embodiment referring to the drawings.

DETAILED DESCRIPTION OF PREFERRED EMBODIMENT

Figure 1:
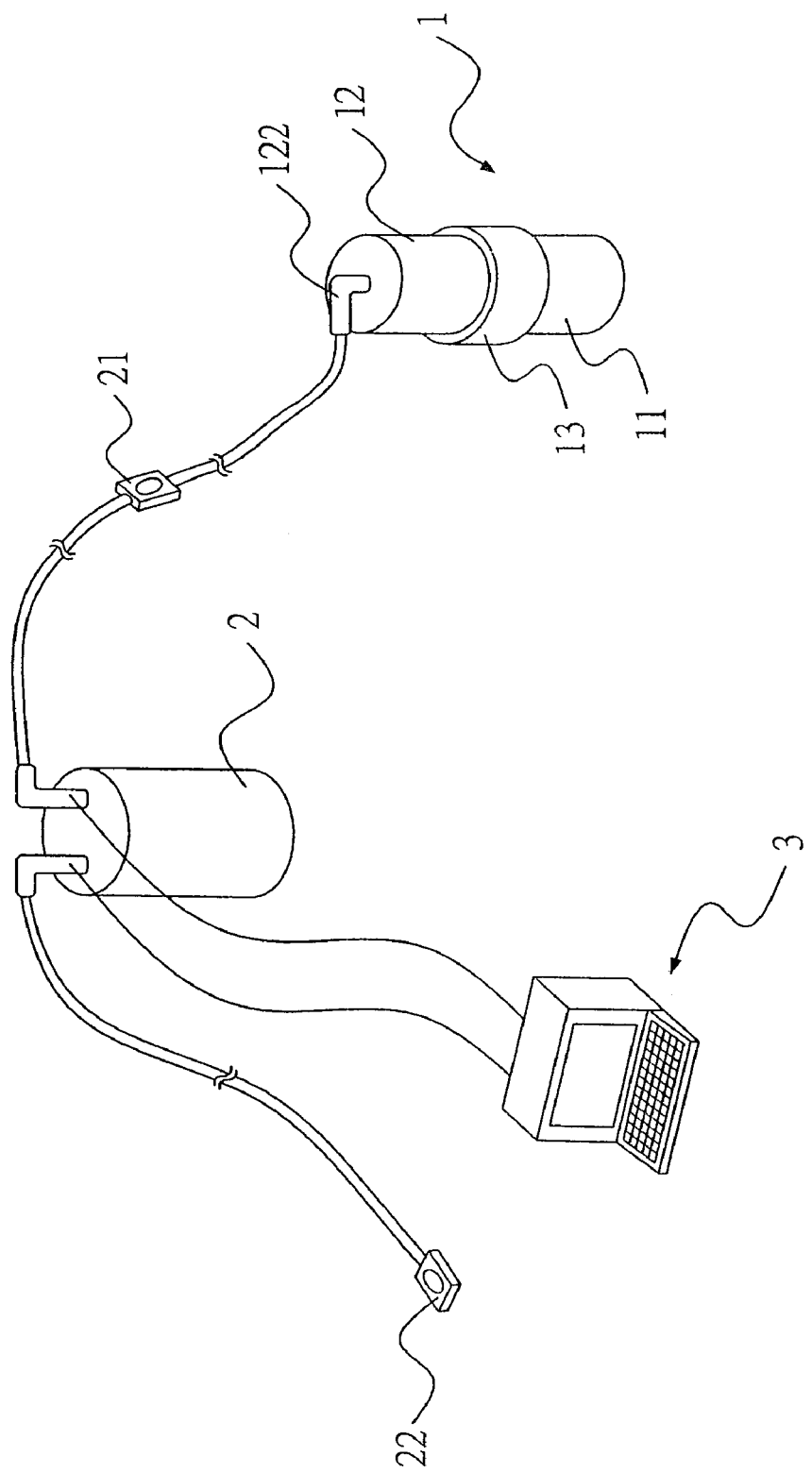
FIG. 1 is a perspective of an apparatus for measuring the permeability of an anode of a solid oxide fuel cell according to the preferred embodiment of the present invention.

Referring to FIG. 1, there is shown an apparatus for measuring the permeability of an anode of a solid oxide fuel cell according to the preferred embodiment of the present invention. The apparatus includes a measuring unit 1, an air reservoir 2 and a recorder 3.

Figure 2:
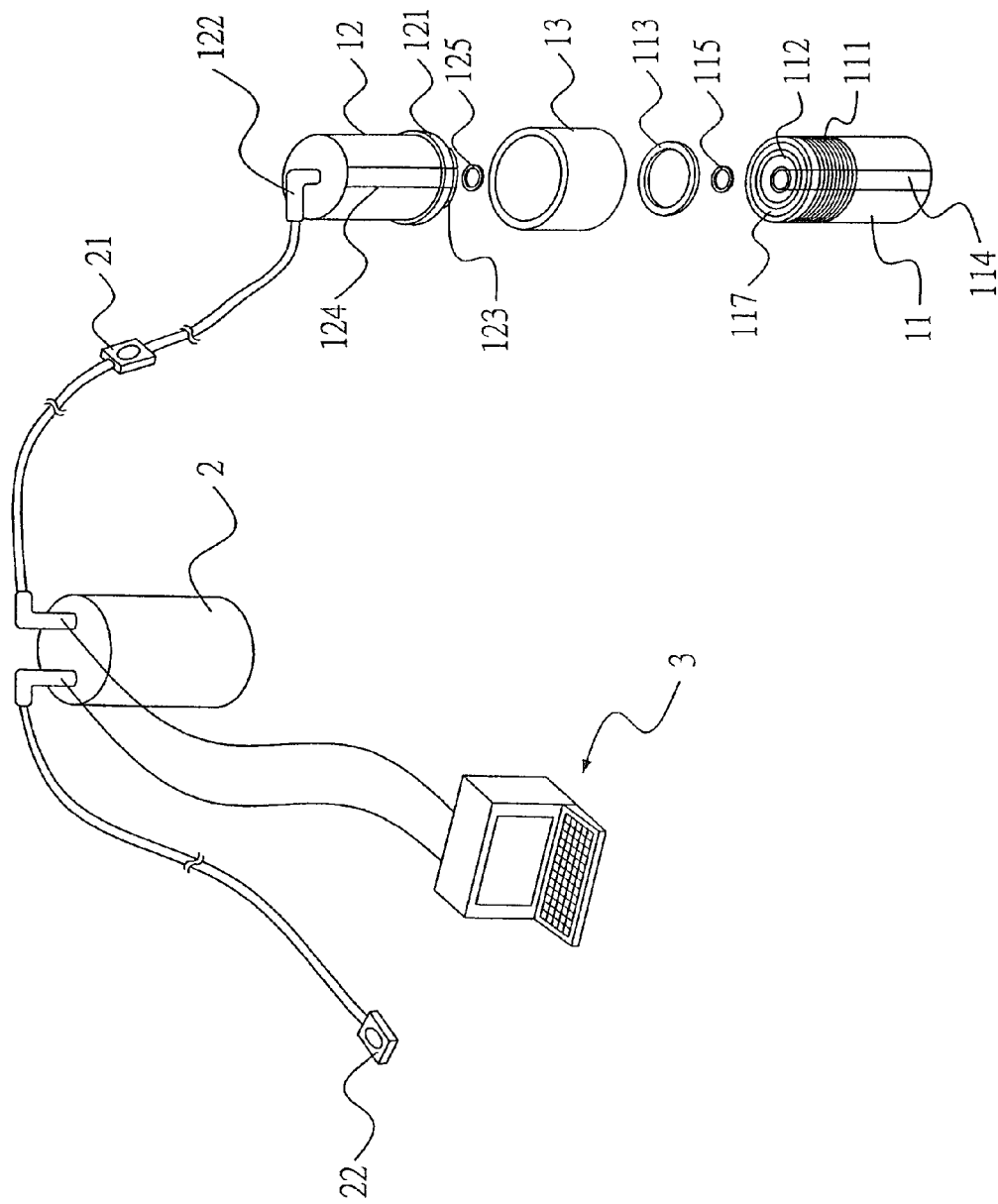
FIG. 2 is an exploded view of the apparatus shown in FIG. 1.
Figure 3:
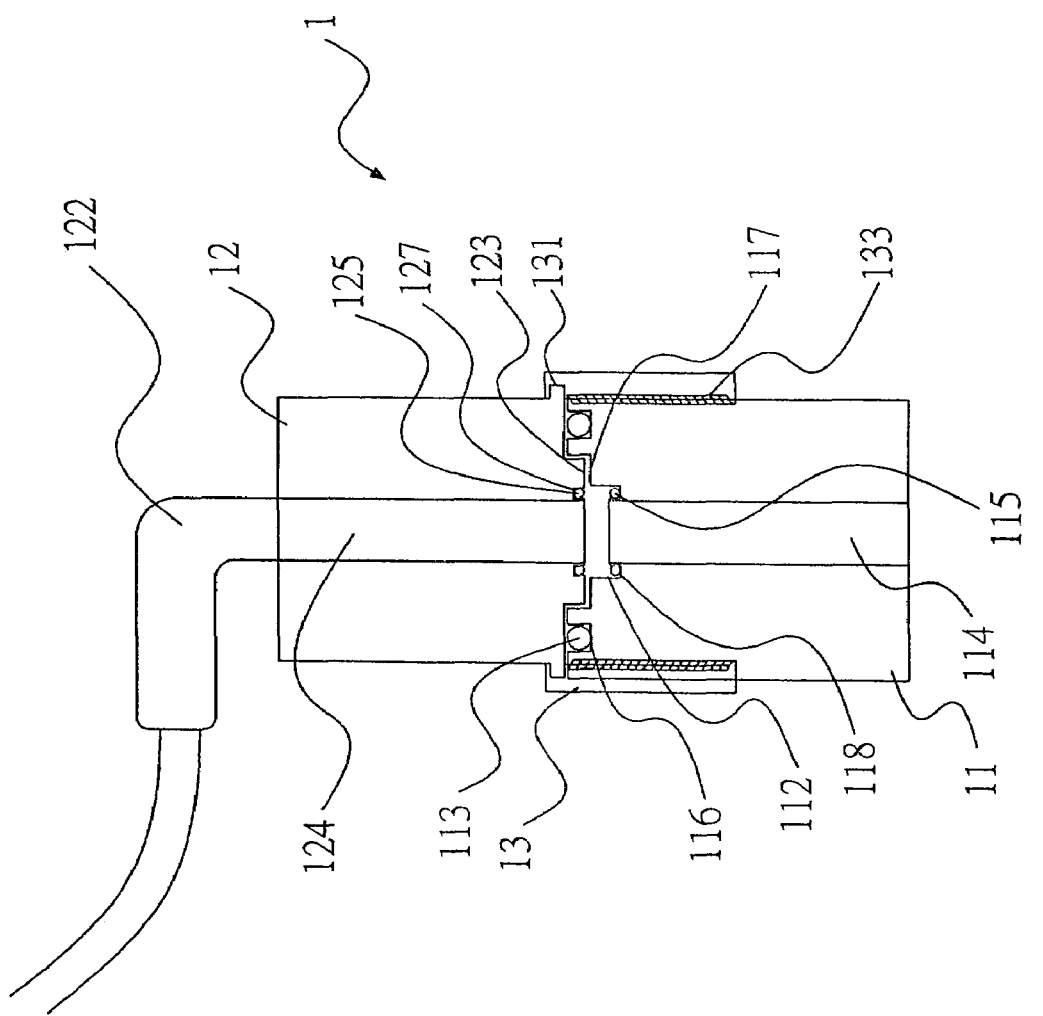
FIG. 3 is a partial, cross-sectional view of the apparatus shown in FIG. 1.

Referring to FIGS. 2 and 3, the specimen container 1 includes a can 11, a cover 12 and a ring 13. The can 11 includes a tunnel 114 defined therein, a large annular groove 116 defined in the top, a large cavity 117 defined in the top and circled by the large annular groove 116, a small cavity 112 defined in the floor of the large cavity 117, a small annular groove 118 defined in the floor of the small cavity 112 and a thread 111 formed on the periphery. A washer 113 is disposed in the large annular groove 116. An annular seal 115 is fit in the small annular groove 118.

The cover 12 includes a tunnel 124 defined therein, a bulger 123 formed on the bottom, an annular groove 127 defined in the bulger 123 around the tunnel 124, an inlet element 122 formed on the top in communication with the tunnel 124 and an annular rib 121 formed on the periphery. An annular seal 125 is fit in the annular groove 127.

The ring 13 includes an annular groove 131 defined in an internal side and a thread 133 formed on the internal side. The annular groove 131 movably receives the annular rib 121 so that the ring 13 is rotationally connected to the cover 12. The thread 133 is for engagement with the thread 111.

The air reservoir 2 includes an inlet element 23 formed on the top and an outlet element 24 formed on the top. A valve 22 is in communication with the inlet element 23 of the air reservoir 2 via a pipe 25. A valve 21 is in communication with the outlet element 24 of the air reservoir 2 through a pipe 26 and in communication with the inlet element 122 of the cover 12 via a pipe 27.

The recorder 3 is connected to the inlet element 23 on one hand and connected to the outlet element 24 on the other hand.

Figure 4:
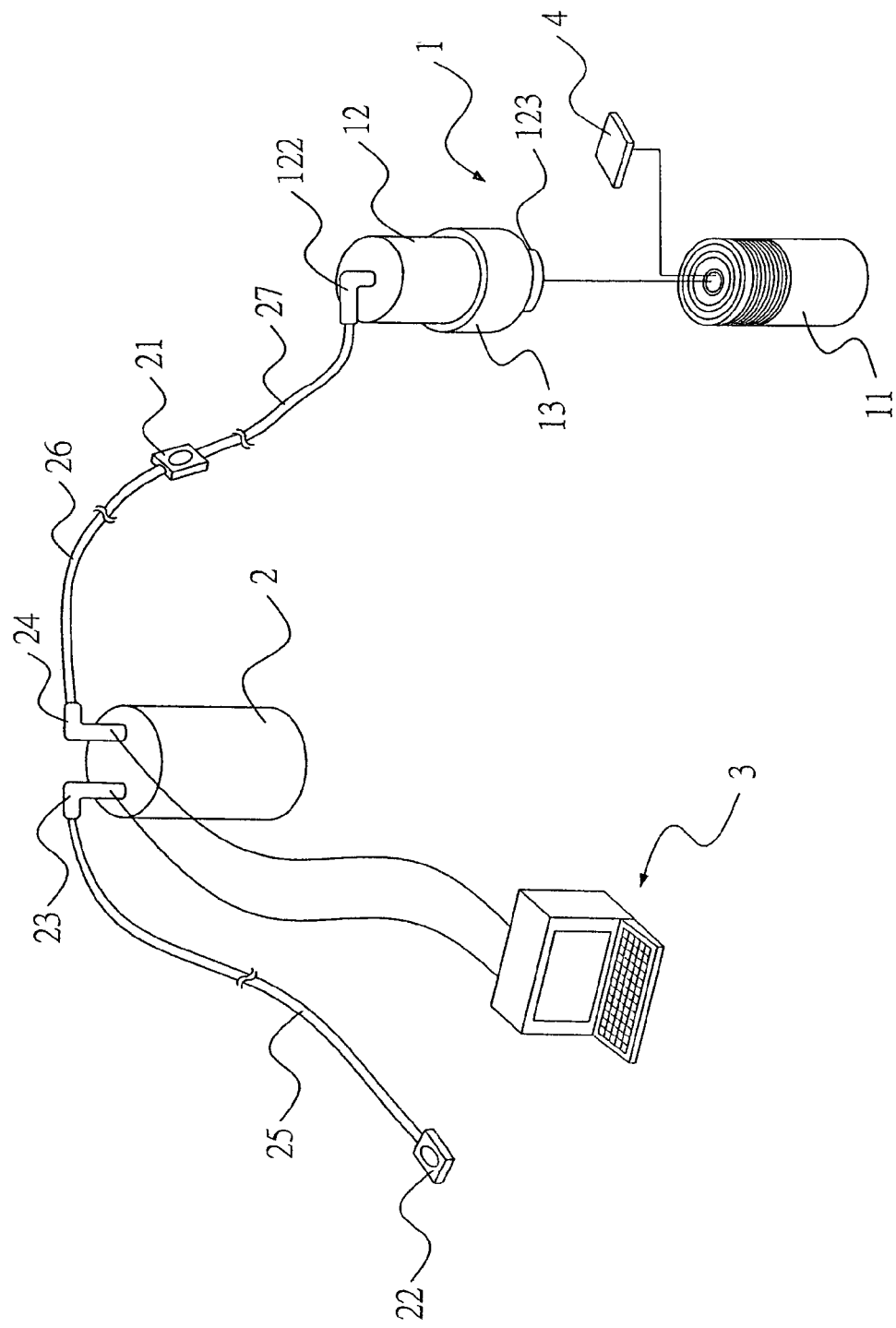
FIG. 4 is a perspective view of an anode and the apparatus shown in FIG. 1.
Figure 5:
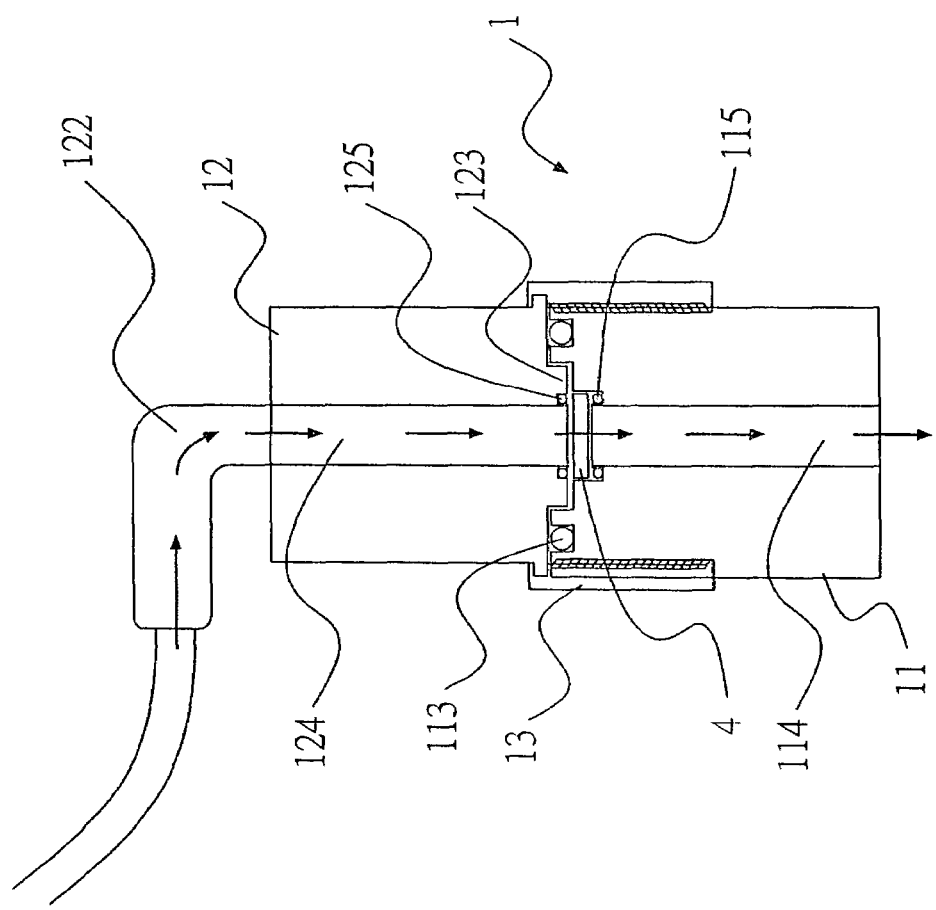
FIG. 5 is a partial, cross-sectional view of the anode and the apparatus shown in FIG. 4.

Referring to FIGS. 4 and 5, an anode 4 for use in a solid oxide fuel cell is disposed in the small cavity 112 of the can 11. The bulger 123 of the cover 12 is disposed in the large cavity 117 of the can 11 so that the anode 4 is located between the annular seals 115 and 125. The thread 133 is engaged with the thread 111. The washer 113 contributes to the firm engagement of the thread 133 with the thread 111. Thus, the ring 13 abuts the cover 12 against the can 11. Accordingly, the annular seal 115 is pressed against the bottom of the anode 4 while the annular seal 125 is pressed against the top of the anode 4.

The valve 22 is opened while the valve 21 is closed. Air is introduced into the air reservoir 2 through the inlet element 23 under the control of the valve 22. The temperature and pressure of the air in the air reservoir 2 are measured and recorded in the recorder 3.

Then, the valve 22 is closed while the valve 21 is opened. The air is introduced into the specimen container 1 from the air reservoir 2 under the control of the valve 21. Some of the air passes through the anode 4. After some time, the temperature and pressure of the air in air reservoir 2 are measured and recorded in the recorder 3 again.

The difference between the temperatures, the difference between the pressures, the period of time and the area of the anode 4 are used to calculate the permeability of the anode 4.

The present invention has been described via the detailed illustration of the preferred embodiment. Those skilled in the art can derive variations from the preferred embodiment without departing from the scope of the present invention. Therefore, the preferred embodiment shall not limit the scope of the present invention defined in the claims.

The invention claimed is:

1. An apparatus for measuring the permeability of an anode of a solid oxide fuel cell, the apparatus comprising:
    a specimen container comprising:
        a can comprising a tunnel defined therein and a cavity in communication with the tunnel, wherein the anode can be disposed in the cavity such that at least a portion of a first side of the anode is sealed; and
        a cover comprising a tunnel defined therein and a bulger inserted in the cavity and pressed against the anode so that air can penetrate the anode and travel into the tunnel of the can from the tunnel of the cover and such that at least a portion of an opposite second side of the anode is sealed and wherein the can connects with the cover such that the anode is fully enclosed by the specimen container;
    an air reservoir in communication with the cover; and
    a recorder for measuring and recording the pressure and temperature of air in the air reservoir before and after the air is introduced into the specimen container from the air reservoir.

2. The apparatus according to claim 1 comprising a ring for connecting the cover to the can.

3. The apparatus according to claim 2, wherein the can comprises a thread formed thereon, and the ring comprises a thread for engagement with the thread of the can.

4. The apparatus according to claim 3, wherein the cover comprises an annular rib formed thereon, and the ring comprises an annular groove for movably receiving the annular rib.

5. The apparatus according to claim 3 comprising a washer provided between the can and the ring.

6. The apparatus according to claim 5, wherein the can comprises an annular ring for receiving the washer.

7. The apparatus according to claim 1 comprising an annular seal disposed in the cavity of the can for pressing against the anode.

8. The apparatus according to claim 1 comprising an annular seal attached to the bulger of the cover for pressing against the anode.

9. The apparatus according to claim 1 comprising a valve for controlling the travel of the air into the air reservoir and another valve for controlling the travel of the air into the specimen container from the air reservoir.

* * * * *